US007204257B2

(12) United States Patent  (10) Patent No.: US 7,204,257 B2
Crossman  (45) Date of Patent: Apr. 17, 2007

(54) DENTAL FLOSS DEVICE

(75) Inventor: Scott Philip Crossman, Rockford, MI (US)

(73) Assignee: Ranir, LLC, Grand Rapids, MI (US)

( * ) Notice: Subject to any disclaimer, the term of this patent is extended or adjusted under 35 U.S.C. 154(b) by 268 days.

(21) Appl. No.: 10/871,967

(22) Filed: Jun. 18, 2004

(65) Prior Publication Data

US 2005/0279379 A1   Dec. 22, 2005

(51) Int. Cl.
  *A61C 15/00*  (2006.01)
(52) U.S. Cl. .................................... 132/323; 132/327
(58) Field of Classification Search ........ 132/321–329, 132/309, 311
  See application file for complete search history.

(56) References Cited

U.S. PATENT DOCUMENTS

| 158,673 | A | * | 1/1875 | Bulkley ..................... 132/309 |
| 682,892 | A | * | 9/1901 | Thurston .................... 132/328 |
| 4,192,330 | A | | 3/1980 | Johnson |
| 4,592,109 | A | * | 6/1986 | Borea et al. ................. 15/172 |
| 5,056,540 | A | | 10/1991 | Page |
| 5,058,230 | A | * | 10/1991 | Hodosh et al. ............. 15/167.1 |
| 5,067,503 | A | | 11/1991 | Stile |
| 5,113,880 | A | * | 5/1992 | Honda et al. ............... 132/321 |
| 5,483,982 | A | * | 1/1996 | Bennett et al. ............. 132/323 |
| 5,738,125 | A | * | 4/1998 | Lin ........................... 132/323 |
| 5,934,295 | A | * | 8/1999 | Gekhter et al. ............ 132/309 |
| 6,145,152 | A | * | 11/2000 | Ward ......................... 15/176.1 |
| 6,752,158 | B1 | * | 6/2004 | Gwen ......................... 132/327 |
| 2003/0098037 | A1 | | 5/2003 | Dougan et al. |

OTHER PUBLICATIONS

Calba Corporation, "FlossAwl—Floss Holders—What you should know about them", downloaded from http://www.allny.com/flossawl/flossholders.html, Mar. 31, 2004, pp. 1-2.
Caune & Caune, Inc., "Swordfloss-Easy Flosing product . . . ", downloaded from http://swordfloss.com, Mar. 31, 2004, p. 1.
"Butler G-U-M Eez-Thru Flossers, Mint", downloaded from http://www.drugstore.com/products, Mar. 31, 2004 pp. 1-3.
"The Auto Flosser battery operated dental flosser for oral care", downloaded from http://www.ballbeauty.com, Mar. 31, 2004, p. 1.
"Flosspro—as quick & easy to use as your toothbrush", downloaded from http://www.flosspro.com, Mar. 31, 2004, pp. 1-3.
Flossaid Corporation, "Makes Flossing Easy!", downloaded from http://flossaid.com/bnewhome.shtml, Mar. 31, 2004, pp. 1-2.

(Continued)

*Primary Examiner*—Todd E. Manahan
*Assistant Examiner*—Rachel A. Running
(74) *Attorney, Agent, or Firm*—Warner Norcross & Judd

(57) ABSTRACT

A dental flosser includes a handle and a dental floss holder releasably received by the handle. The dental floss holder includes a base, a pair of arms for holding a length of dental floss, and a toothpick extending from the base. The handle includes a receiver in which the toothpick on the dental floss holder is received. The handle and the dental floss holder cooperate to prevent transverse movement of the dental floss holder.

17 Claims, 4 Drawing Sheets

OTHER PUBLICATIONS

Floss Boss Inc., "Flossing Made Easy!", downloaded from http://www.flossbossinc.com, Mar. 31, 2004, p. 1.

"Oral-B Hummingird Starter Set", downloaded from http://www.drugstore.cm/products, Mar. 31, 2004 pp. 1-2.

"Glide Floss Holder", downloaded from http://www.glidefloss.com/flossholder.html, Mar. 31, 2004, p. 1.

"Xylifloss Pocket Dental Flosser, Mint Flavored", downloaded from http://www.drugstore.com/products, Mar. 31, 2004, pp. 1-3.

"Butler GUM Oral Care—Floss", downloaded from http://www.dentist.net/butler-floss.asp, Mar. 31, 2004, pp. 1-2.

"US Dentek Flossing & Denture Oral Care", downloaded from http://www.dentist.net/breath-remedy-3.asp, Mar. 31, 2004, pp. 1-3.

"Flossbrite—A revolution in dental floss, flossing, and oral care", downloaded from http://www.flossbrite.com, Mar. 31, 2004, pp. 1-2.

* cited by examiner

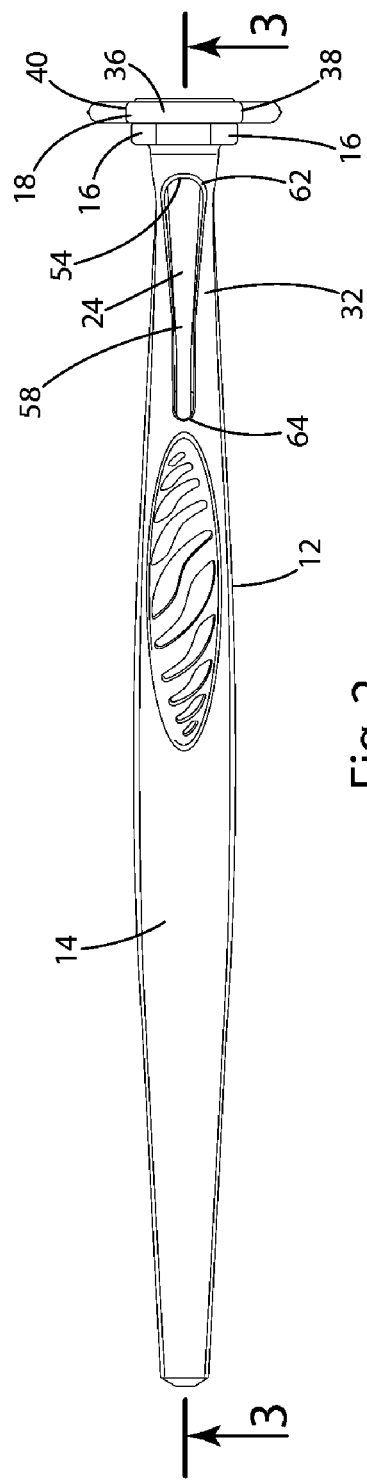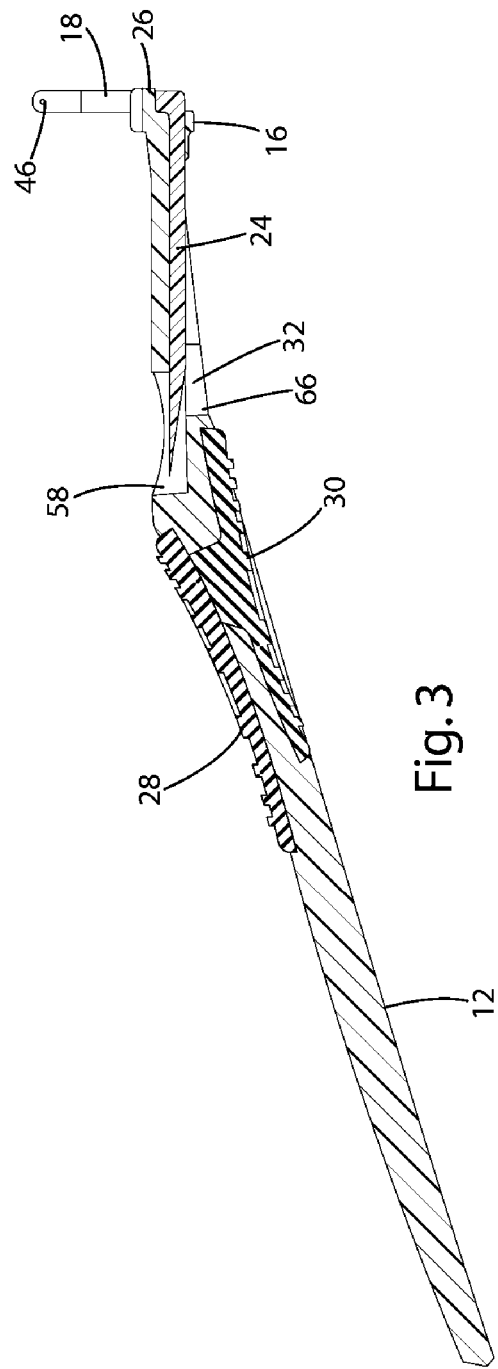

DENTAL FLOSS DEVICE

BACKGROUND OF THE INVENTION

The present invention relates to dental floss devices, and more particularly to dental flossers having a handle and a disposable dental floss holder.

A dental flosser includes an easy to use handle and a disposable dental floss holder that attaches to one end of the handle. The handle portion resembles the handle of a toothbrush, and includes a head portion that receives the dental floss holder.

An example a dental flosser is shown in U.S. patent application 2003/0098037 to Dougan et al, published May 29, 2003. Dougan shows a device (1) with a handle (2) having a head (3), and a disposable dental floss holder (4) that attaches to the head (3). The dental floss holder (4) includes a base portion (20) and a pair of jaws (21) extending from the base portion (20) for holding a length of dental floss (5). The dental floss holder (4) snap-fits into the head (3) by fitting the base (20) into a vertical notch in the head (3).

Unfortunately, Dougan suffers from disadvantages. For instance, if too much pressure is applied during flossing, the dental floss holder could accidentally disengage from the notch in the handle, making it difficult to floss and potentially injuring the user. Attempts to increase the force required to disengage the dental floss holder have the undesirable side effect of making it harder for a user to remove and dispose the dental floss holder after use. In addition, slight tolerance variations in the formation of the dental floss holder or changes in the size of the holder after formation (such as warping) can make it difficult to maintain tension in the dental floss—which is necessary for the device to function properly.

SUMMARY OF THE INVENTION

The aforementioned problems are overcome by the present invention wherein a dental flosser includes a handle and a dental floss holder mounted longitudinally within the handle to prevent transverse movement of the holder within the handle. More specifically, the holder includes an integral toothpick, and the handle includes a longitudinally opening receiver in which the toothpick is releasably fitted.

In the current embodiment, the receiver is a bore extending into the handle. The handle includes a transverse opening communicating with the bore, and the toothpick includes a detent fitted within the opening to aid in retaining the dental floss holder on the handle.

The longitudinally opening receiver prevents the dental floss holder from moving transversely with respect to the handle while in use. And, the inclusion of a toothpick within the flosser provides users with an additional feature.

These and other objects, advantages, and features of the invention will be more fully understood and appreciated by reference to the detailed description of the current embodiment and the drawings.

BRIEF DESCRIPTION OF THE DRAWINGS

FIG. 2 is a top plan view of the dental flosser.
FIG. 3 is a cross-sectional view of the dental flosser along line 3—3 in FIG. 2.

DETAILED DESCRIPTION OF THE CURRENT EMBODIMENT

Figure 1:
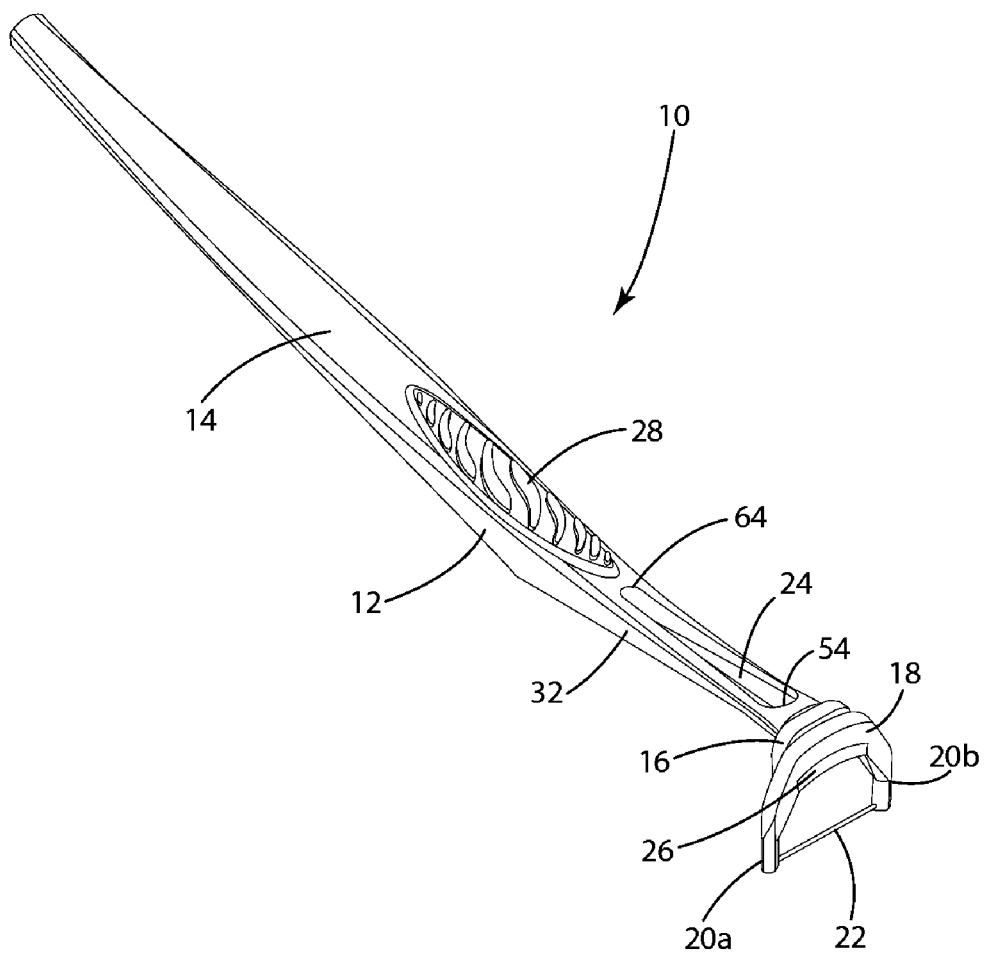
FIG. 1 is a perspective view of the dental flosser.

A dental flosser in accordance with one embodiment of the present invention is shown in FIG. 1, and generally designated 10. The device 10 generally includes a handle 12 having a shaft 14 and a head 16, and a dental floss holder 18 that can be removably attached to the handle 12. The dental floss holder 18 generally includes a pair of arms 20a–b for holding a length of dental floss 22, and a toothpick 24.

Figure 6:
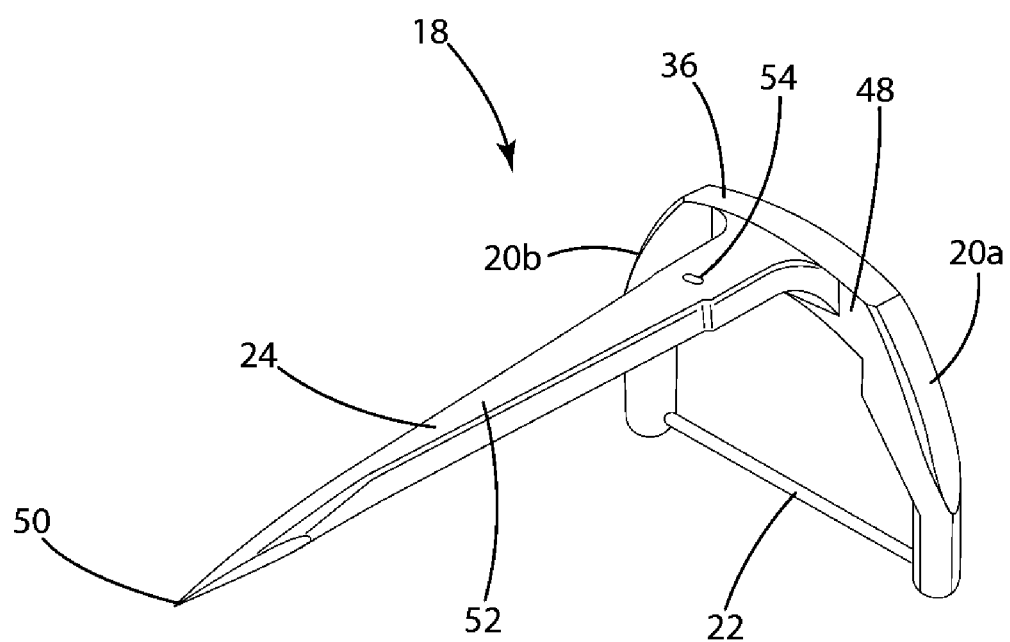
FIG. 6 is a perspective view of the dental floss holder.

The dental floss holder 18 is generally a molded thermoplastic that may be disposable. The dental floss holder may include a base 36 having opposite ends 38, 40 and arms 20a–b extending downwardly from the base 36 at or near the opposite ends 38, 40. The arms 20a–b include inner edges 42a–b that may be tapered for added strength, and further include ends 44a–b. A length of dental floss yarn 22 is generally molded in place to the ends 44a–b of the arms 20a–b. Alternatively, a variety of conventional methods may be used to hold the dental floss on the arms 20a–b, such as wrapping the floss 22 around each of the ends 44a–b. In one embodiment, the dental floss holder 18 also includes a toothpick 24. As shown in FIG. 6, the toothpick 24 extends from the rear surface 48 of the base 36 approximately perpendicular to the base 36. The toothpick 24 generally extends outward to form a pointed end 50. The toothpick may further include an upper surface 52 that includes a small bump or protuberance 54. As described below, the bump 54 aids in retaining the dental floss holder 18 on the handle 12.

The dental floss 22 may be one of a wide variety of known multi-filament or monofilament yarns, including, but not limited to, nylon, PTFE, EPTFE, polyethylene, ultra high molecular weight polyethylene, polypropylene. The yarn may be colored or flavored, and may include one or more functional coatings such as abrasives, antioxidants, anti-inflammatory, anti-caries, anti-plaque, and desensitizing agents.

Figure 5:
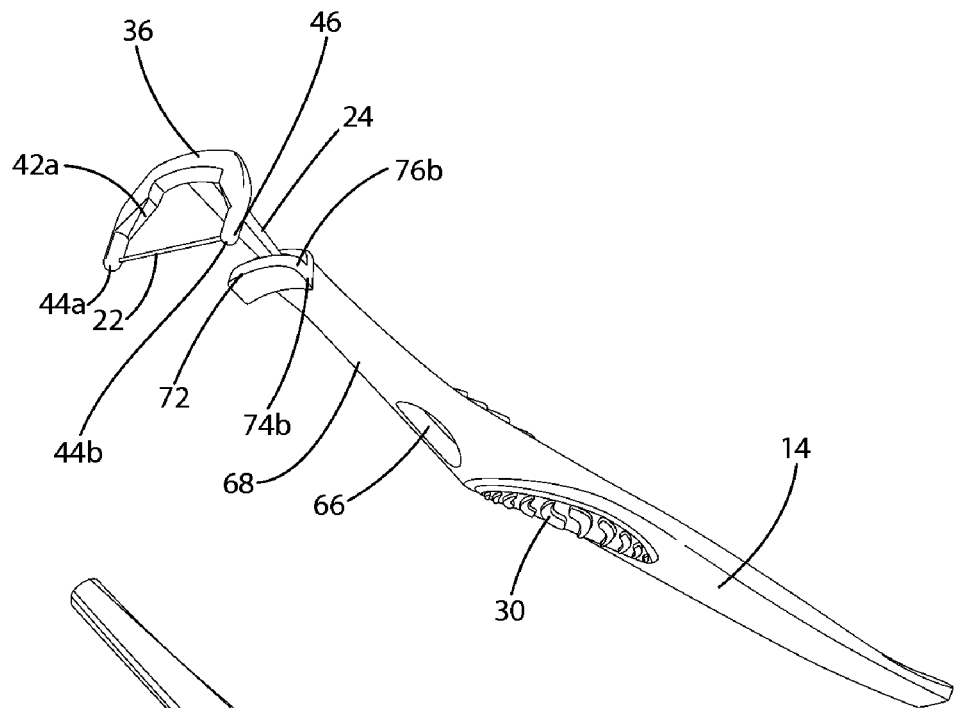
FIG. 5 is a bottom perspective view of the dental flosser with the dental floss holder partially removed.
Figure 4:
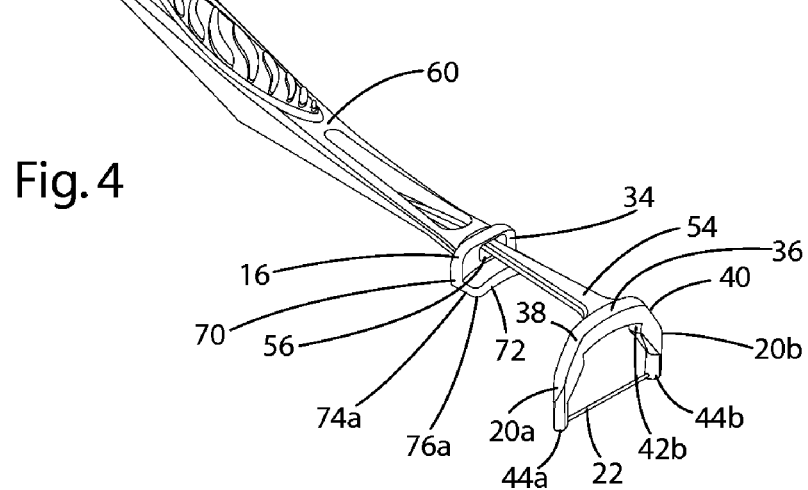
FIG. 4 is a top perspective view of the dental flosser with the dental floss holder partially removed.

The handle 12 is generally a molded thermoplastic that is shaped and contoured for ease of holding and use by the user. The handle 12 may include upper 28 and lower 30 grips that are formed from any of a variety of materials, such as rubber, and attached to the shaft 14 for additional ease of use. As shown, the shaft 14 defines a generally longitudinal direction, and includes a neck 32 in front of the grips 28 and 30 that supports the head 16. The head 16 is also generally a molded thermoplastic, which may be integrally formed with the rest of the handle 12, or may be formed as a separate piece and conventionally attached to the handle 12. Referring now to FIGS. 4 and 5, the head 16 includes a receiver that cooperates with the dental floss holder 18. In the illustrated embodiment, the head 16 includes a face 34 that defines a bore 56 approximately in the center of the face 34. The bore 56 extends through the head 16, and through at least a portion of the neck 32 of the shaft 14. The depth of the bore 56 is approximately the same as the length of the toothpick 24. Of course, while the illustrated embodiment shows a bore, the head 16 may include any type of aperture, such as a hole or a slot or the like for receiving the toothpick 24. The handle 12 may also define an opening 58 that exposes a portion of the bore 56. As shown, the opening 58 is a cutout in the upper surface 60 of the shaft 14 that extends along substantially all of the neck portion 32 of the shaft 14 from a front edge 62 near the head 16 to a rear edge 64 near the upper grip 28. The handle 12 may further define another opening 66 in the lower surface 68 of the shaft 14. The opening 66 may be smaller than the upper opening 58, and also exposes a portion of the bore 56. In one embodiment, the handle 16 may further include a tabular protrusion 26 extending from the face 34. As shown, the protrusion 26 extends from the face 34 along approximately the entire lower edge 70 of the face 34. The width of the protrusion 26 is slightly larger that the distance between the inner surfaces 42a–b of the arms 20a–b. The protrusion 26 includes a front surface 72, and opposing side edges 74a–b. The front surface 72 and side edges 74a–b are joined by corners 76a–b that may be prov In operation, the dental floss holder 18 may be removably attached to the handle 12. In one embodiment, the dental floss holder 18 attaches to the handle 12 by inserting the toothpick 24 into the bore 56. The dental floss holder 18 is inserted until the rear surface 48 of the dental floss holder 18 abuts the face 34 of the handle 12. When inserted, the toothpick 24 may be visible through both the upper opening 58 and the lower opening 66. The bump 54 is positioned such that when the dental floss holder 18 is inserted, the bump 54 engages the front edge 62 of the upper opening 58 and retains the holder 18 in the handle 12. Alternatively, the bump 54 may be located on the shaft 14 and the holder 18 may include a small recess (not shown) that may similarly engage to retain the holder 18. The bump 54 may also be located on a different surface of the toothpick 24, such as the lower surface. In addition, the tabular protrusion 26 acts to spread the arms 20a–b and therefore apply tension to the length of dental floss 22 when the dental floss holder 18 is engaged with the handle 12. Since the width of the tabular protrusion 26 is slightly larger than the distance between the arms 20a–b, the protrusion forms a press-fit with the inner surfaces 42a–b of the arms and pushes the arms 20a–b outward.

The above descriptions are those of current embodiments of the invention. Various alterations and changes can be made without departing from the spirit and broader aspects of the invention, which are to be interpreted in accordance with the principles of patent law including the Doctrine of Equivalents.

The embodiments of the invention in which an exclusive property or privilege is claimed and defined as follows:

1. A dental flosser comprising:
   a dental floss carrier including dental floss, a U-shaped floss holder having a base and a pair of arms extending from said base, and a toothpick extending generally perpendicularly from said floss holder, said toothpick including a bump; said arms supporting said dental floss, and
   a handle including a shaft and a head, said shaft defining a longitudinal direction, said handle including a terminal transverse face defining a longitudinal receiver opening, said handle including a protrusion extending longitudinally outwardly from said face, said toothpick received and releasably retained within said receiver opening in said longitudinal direction by engagement of said bump with said handle, said protrusion engaging and cooperating with said base and both of said arms of said floss holder to prevent transverse movement and rotational movement of said dental floss holder with respect to said handle.

2. The dental flosser of claim 1 wherein said tabular protrusion interfits between said pair of arms when said dental floss holder cooperates with said base, whereby said arms are spread to apply tension to said length of dental floss.

3. The dental flosser of claim 1 wherein said head includes a face, said receiver defining a bore that extends through said face and a portion of said shaft, at least a portion of said toothpick extending into said bore when said dental floss holder cooperates with said head.

4. The dental flosser of claim 3 wherein said shaft defines an opening that exposes a portion of said bore and includes a front edge , said protuberance positioned such that it engages said front edge to retain said dental floss holder on said head when said dental floss holder cooperates with said head.

5. The dental flosser of claim 4 wherein said shaft includes an upper surface, said upper surface defining said opening.

6. The dental flosser of claim 5 wherein said front edge is located proximate said head.

7. The dental flosser of claim 6 wherein said shaft includes a lower surface, said lower surface defining an opening exposing a portion of said bore.

8. A dental flosser comprising:
   a handle having a shaft and a head, said shaft defining a longitudinal direction, said head including a terminal transverse face, said handle defining a toothpick opening, said opening extending through said face and oriented generally in the longitudinal direction, said face including a tabular protrusion extending longitudinally outwardly therefrom, said tabular protrusion including first and second side edges; and
   a dental floss carrier including dental floss, a U-shaped floss holder having a base and a pair of arms extending from said base and supporting said dental floss, and a toothpick extending generally perpendicularly from said base and into said toothpick opening, said toothpick including a bump extending therefrom, said tabular protrusion interfitting between said arms, said bump engaging said toothpick opening.

9. The dental flosser of claim 8 wherein said toothpick opening is a bore that extends through said face and a portion of said shaft, a portion of said toothpick extending into said bore when said dental floss holder is received by said head.

10. The dental flosser of claim 9 wherein said shaft defines an aperture that exposes a portion of said bore and includes a front edge, and said bump positioned such that it engages said front edge of said aperture to retain said dental floss holder on said head when said dental floss holder is received by said head.

11. The dental flosser of claim 10 wherein said shaft includes an upper surface, said upper surface defining said aperture.

12. The dental flosser of claim 11 wherein said front edge is located proximate said head.

13. The dental flosser of claim 12 wherein said shaft includes a lower surface, said lower surface defining an aperture exposing a portion of said bore.

14. A dental floss device comprising:
   a handle including a shaft portion and a head portion, said shaft portion extending in a longitudinal direction, said head portion including a terminal transverse face, said face defining a bore that extends through said face and into a portion of said shaft, said face including a tabular protrusion extending longitudinally outwardly from said face; and a dental floss carrier including dental floss, a dental floss holder having a base, said base including a pair of arms extending from said base and supporting said dental floss, said dental floss carrier further including a toothpick extending generally perpendicularly from said base, and a bump extending from said toothpick, said dental floss device being removably engaged with said handle such that said toothpick may be inserted in said longitudinal direction into said bore defined by said face, said bump retaining said dental floss carrier in said longitudinal direction, said tabular protrusion interfitting between said pair of arms to prevent movement of said dental floss holder and to spread said arms and apply tension to said length of dental floss.

15. The dental floss device of claim 14 wherein said engagement of said dental floss holder and said handle is a press-fit.

16. The dental floss device of claim 14 wherein said shaft defines an opening that exposes a portion of said bore and includes a front edge, and said bump engages said front edge when said dental floss holder is engaged with said handle to retain said dental floss holder on said handle.

17. The dental floss device of claim 16 wherein said shaft includes an upper surface, said opening defined in said upper surface.

* * * * *